United States Patent
Wu

(10) Patent No.: US 10,932,900 B2
(45) Date of Patent: Mar. 2, 2021

(54) METHOD OF SUTURELESS INTRASCLERAL HAPTIC-HOOK LENS IMPLANTATION

(71) Applicant: THE EYE HOSPITAL OF WENZHOU MEDICAL UNIVERSITY, Wenzhou (CN)

(72) Inventor: Ronghan Wu, Wenzhou (CN)

(73) Assignee: THE EYE HOSPITAL OF WENZHOU MEDICAL UNIVERSITY, Wenzhou (CN)

( * ) Notice: Subject to any disclaimer, the term of this patent is extended or adjusted under 35 U.S.C. 154(b) by 0 days.

(21) Appl. No.: 16/396,286

(22) Filed: Apr. 26, 2019

(65) Prior Publication Data

US 2020/0337832 A1    Oct. 29, 2020

(51) Int. Cl.
*A61F 2/16* (2006.01)
*A61F 9/013* (2006.01)
*A61F 9/00* (2006.01)

(52) U.S. Cl.
CPC .............. *A61F 2/16* (2013.01); *A61F 9/013* (2013.01); *A61F 9/0017* (2013.01); *A61F 2002/1683* (2013.01)

(58) Field of Classification Search
CPC ............ A61F 9/0017; A61F 2250/0091; A61F 2220/0008; A61F 2/16; A61F 2/1662–1672
USPC ......................................................... 606/107
See application file for complete search history.

(56) References Cited

U.S. PATENT DOCUMENTS

| 4,406,285 A | * | 9/1983 | Villasenor | A61F 9/013 33/1 B |
| 4,702,244 A | * | 10/1987 | Mazzocco | A61F 2/1602 606/107 |
| 4,750,498 A | * | 6/1988 | Graham | A61F 2/1662 600/587 |
| 4,769,034 A | * | 9/1988 | Poley | A61F 2/1616 606/166 |

(Continued)

FOREIGN PATENT DOCUMENTS

RU    2192825 C1 * 11/2002

OTHER PUBLICATIONS

English language abstract of Russian patent No. RU-2192825. (Year: 2002).*

(Continued)

*Primary Examiner* — Paul B Prebilic
(74) *Attorney, Agent, or Firm* — Christensen, Fonder, Dardi & Herbert PLLC

(57) ABSTRACT

A method of sutureless intrascleral haptic-hook lens implantation which improves the fixation process of the lens haptics, allowing the lens haptics to be bent and folded back into the vitreous cavity to generate a better stability, avoiding the complication of intrascleral fixation haptic slippage, meanwhile forming a sclera lamellar groove between two adjacent scleral incisions to bury the lens haptics. The method may be adapted to patients in need of intraocular lens implantation without sufficient capsular support, such as aphakia, intraocular lens, lens dislocation, etc. This method enhances the stability and centrality of the lens, the surgical procedures are simple and easy to master, which reduces the operation time.

8 Claims, 9 Drawing Sheets

(56) References Cited

U.S. PATENT DOCUMENTS

| | | | | |
|---|---|---|---|---|
| 4,871,363 | A * | 10/1989 | Kelman | A61F 2/1602 623/6.54 |
| 5,026,393 | A * | 6/1991 | Mackool | A61F 2/16 606/107 |
| 5,108,776 | A * | 4/1992 | Goldberg | A61F 2/16 427/2.24 |
| 5,395,378 | A * | 3/1995 | McDonald | A61B 17/29 606/107 |
| 2014/0039510 | A1 * | 2/2014 | van Saarloos | A61B 3/0025 606/107 |
| 2016/0022488 | A1 * | 1/2016 | Dimmig | A61F 9/007 606/107 |

OTHER PUBLICATIONS

Bedda et al, "Evaluation of suturless scleral fixation with posterior chamber foldable intraocular lens implantation", (Aug. 18, 2019), Int. J. Ophthalmology, vol. 12, pp. 1283-1289. (Year: 2019).*

Ibrahim et al, "The Balanced Two-String Technique for Sulcus Intraocular Lens Implantation in the Absence of Capsular Support", (Jan. 2015), Hindawi Publishing Corp., Journal of Ophthalmology, vol. 2015, pp. 1-5. (Year: 2015).*

Kawaji et al, "Sutureless intrascleral intraocular lens fixation with lamellar dissection of scleral tunnel", (Jan. 2016), Dove Press, Clinical Ophthalmology, pp. 227-231. (Year: 2016).*

Liu et al, "New two-point scleral-fixation technique for foldable intraocular lenses with four hollow haptics", (Mar. 2016), Int. J. Ophthalmology, vol. 9, No. 3, pp. 469-471. (Year: 2016).*

Tian et al, "Capture of intraocular lens optic by residual capsular opening in secondary implantation: long-term follow-up", (2018) BMC Ophthalmology, 18:84, pp. 1-7. (Year: 2018).*

Walia et al "No Suture No Glue Technique of Scleral Fixated IOL (SFIOL) Implantation for Management of Aphakia", (Mar. 2018), Journal of Medical Science and Clinical Research, IGM Publication, vol. 06, Issue 03, (Year: 2018).*

Yamane et al, "Flanged Intrascleral Intraocular Lens Fixation with Double-Needle Technique", (Mar. 2017), American Academy of Ophthalmology, Elsevier, Inc., pp. 1-7. (Year: 2017).*

* cited by examiner

METHOD OF SUTURELESS INTRASCLERAL HAPTIC-HOOK LENS IMPLANTATION

TECHNICAL FIELD

The present invention pertains to the technical field of ophthalmic surgery, and specifically pertains to a method of sutureless intrascleral haptic-hook lens implantation

BACKGROUND

Over the development of intraocular lens suspension in recent years, a number of new technologies and methods have been derived, ranging from the traditional suture fixation to scleral fixation emerged in recent 2 years, with continuous progress and development. The scleral fixation has incomparable advantages compared to the suture fixation: no suture exposure, no suture fracture, small possibility of lens offset, simple operation and less time consuming, reduction of intra-operative iatrogenic injuries. There are many methods for intrascleral fixation, the main difference among which focus on different treatments to lens haptic. Agarwal and Oh et al. have proposed a method of covering lens haptics with scleral flaps, with the aid of biological glue. Takayama K et al. have proposed a method of embedding lens haptics into intrascleral tunnels other than below scleral flaps, which possesses a better stability. Ohta T et al. have invented a Y-shaped scleral incision for the lens haptic fixation, meanwhile the tightness of the incision has been enhanced.

However, there were also certain inadequacies in the intrascleral fixation: on the one hand, the operation was a little complicated, the length and depth of intrascleral tunnels were difficult to control, and there was the possibility of scleral flap fracture; on the other hand, there was a chance of intraocular lens haptic slippage, thus causing lens offset, even dislocation, etc.

SUMMARY

To overcome the defects in the prior art, the present invention provides a method of sutureless intrascleral haptic-hook lens implantation.

The technical solution employed in the present invention is: a method of sutureless intrascleral haptic-hook lens implantation, comprising the following steps:

(1) for subjects not undergoing vitreous surgery, conventional vitrectomy or anterior vitrectomy was conducted in advance, a lateral corneal incision 1 was made and a perfusion tube 100 was inserted into the anterior chamber 401, two opposing conjunctival incisions 103 of 3.0 mm, symmetrical at 180°, were cut on the conjunctiva 102 outside the margin of cornea 104;

(2) two puncture openings 2 were made at 1.5-2.0 mm outside the margin of cornea 104 with a 26 G pinhead, forming two puncture channels 201, the spacing distance between the two puncture openings 2 was 1 mm, the puncture openings 2 were parallel to the margin of cornea 104 and formed an angle of 30° with the surface of the sclera, the puncture directions of the two puncture openings 2 were opposite, making the puncture channels 201 profiled in a splayed pattern, and a lamellar sclera incision 202 was cut in the distance of 1 mm between the two puncture openings 2, forming a groove 3;

(3) the same operations as those in step (2) were conducted at the 180° symmetrical sides of the opposing corneas 104 at the two puncture openings 2 of step (2), forming two puncture openings 2 at the other side and the groove 3 between them, the puncture openings 2 at the two places and the grooves 3 between them were set symmetrically at 180°;

(4) a main corneal incision 4 of 3.0 mm was made over the cornea 104, through which the intraocular lens 403 was pushed into the anterior chamber 401, leaving one haptic 5 outside the main corneal incision 4, a 25 G membrane forceps 402 went into the eye from the puncture opening 2 on one side, grasping one haptic 5 of the intraocular lens 403 and pulling it out of the eye through one puncture opening 2, similarly the other haptic 5 of the intraocular lens 403 was grasped from the puncture opening 2 on the other side and pulled out of the eye through the puncture opening 2 on this side;

(5) the haptic 5 fixed outside the eye was bent and then folded back into the vitreous chamber 501 through the adjacent puncture opening 2, just leaving the haptic 5 of the intraocular lens 403 exposed outside the sclera embedded in the groove 3 formed by the lamellar sclera incision 202 between two adjacent puncture openings 2, the haptic 5 was adjusted to make the intraocular lens 403 to be centered;

(6) the perfusion tube 100 was removed, the main corneal incision 4 was watertight, the conjunctival incisions 103 were sewed with absorbable suture to complete the implantation and fixation of the intraocular lens 403.

The two pairs of puncture openings 2 set symmetrically opposing at 180° were set at the positions of 4 o'clock and 10 o'clock on the clock dial respectively.

The conjunctival incisions 103 set symmetrically opposing at 180° were set at the positions of 4 o'clock and 10 o'clock on the clock dial respectively.

The intraocular lens 403 was a 3-pieces posterior chamber intraocular lens, the haptic 5 of which employed polyvinylidene fluoride (PVDF) as the support, the haptic 5 was in a C shape, which formed an angle of 5° with the lens body.

The closed conjunctival incisions 103 in step (6) were sewed or closed by electrocoagulation.

The puncture openings 2 in step (2) formed an angle of 30° with the surface of the sclera, making the puncture channels 201 profiled in a splayed pattern.

The present invention has the following benefits: the present invention provides a method of sutureless intrascleral haptic-hook lens implantation, which improves the fixation process of the lens haptics, allowing the lens haptics to be bent and folded back into the vitreous chamber to generate a better stability, avoiding the complication of intrascleral fixation haptic slippage, meanwhile forming a sclera lamellar groove between two adjacent scleral incisions to bury the lens haptics, which method may be adapted to patients in need of intraocular lens implantation while without sufficient capsular support, such as aphakia, lens or intraocular lens dislocation, etc. This method enhances the stability and centrality of the lens, the surgical procedures are simple and easy to master, which reduces the operation time. In the cases implemented currently, we have not found the complications such as incision leakage, retinal detachment, endophthalmitis, tilt or dislocation of the intraocular lens, vitreous hemorrhage, and the like, and the postoperative visual acuities of patients have been significantly improved.

Figure 1:
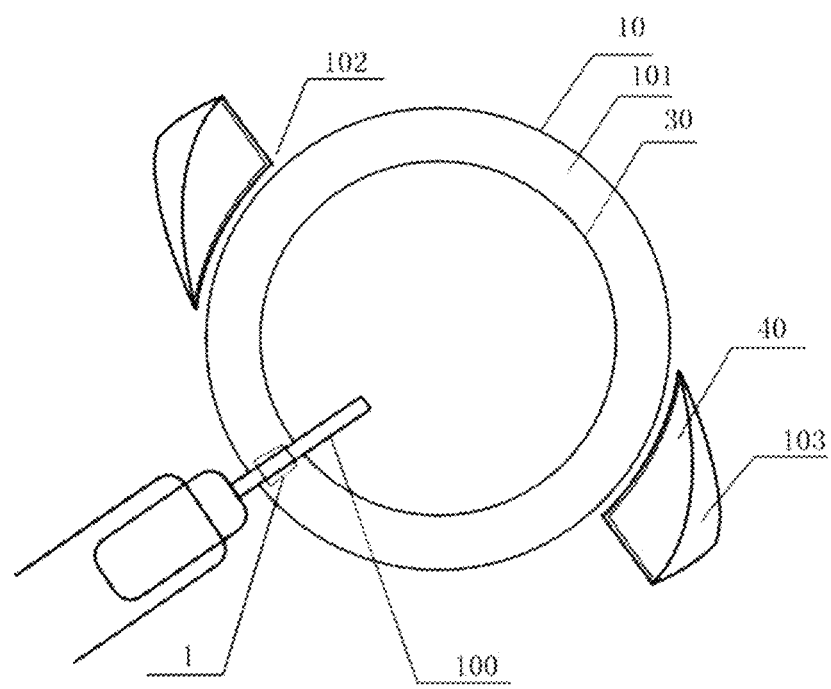
FIG. 1 is the graphical representation of surgical procedures of the present invention.

Wherein, the reference numerals correspond as follows: 1—lateral corneal incision, 2—puncture opening, 3—groove, 4—main corneal incision, 5—haptic, 10—corneal limbus, 16—ciliary body, 30—pupillary margin, 40—sclera, 100—perfusion tube, 101—iris, 102—conjuctiva, 103—conjunctival incision, 104—cornea, 201—puncture channel, 202—lamellar sclera incision, 401—anterior chamber, 402—membrane forceps, 403—intraocular lens, 501—vitreous chamber.

Figure 7A:
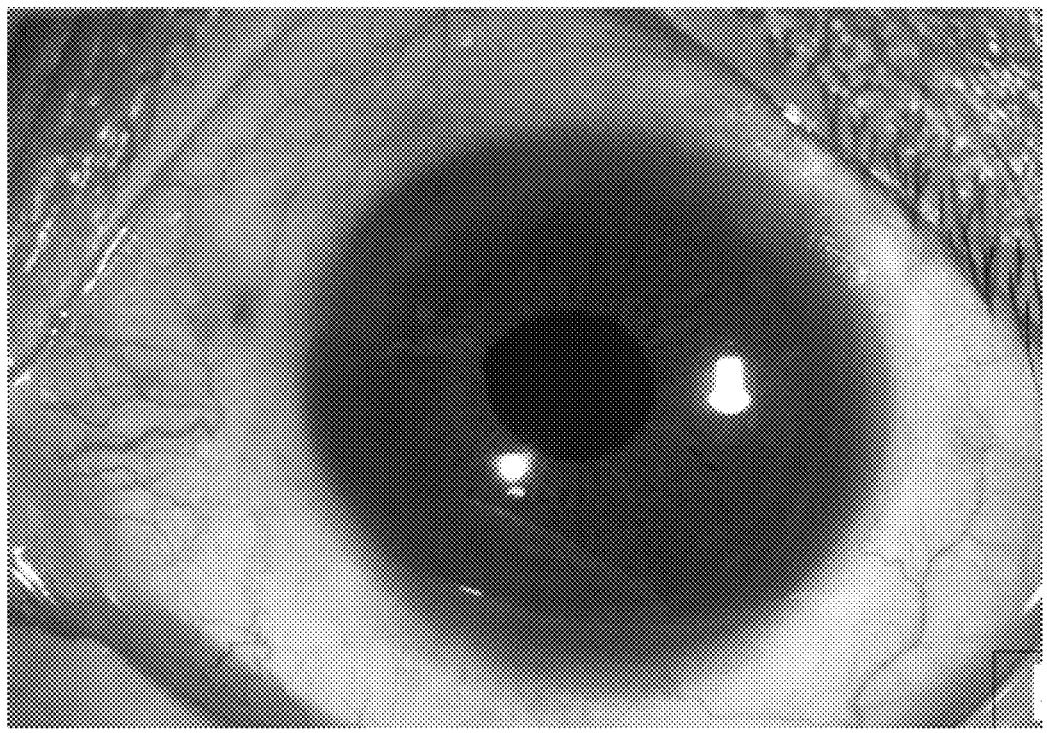
Figure 7B:
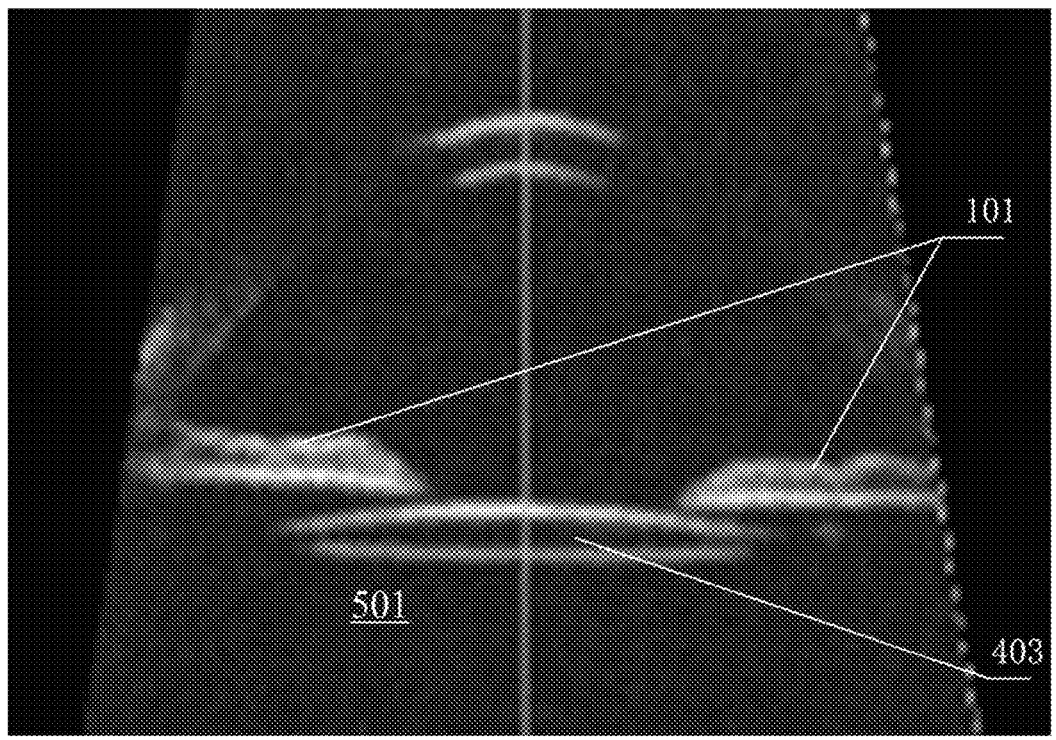
Figure 7C:
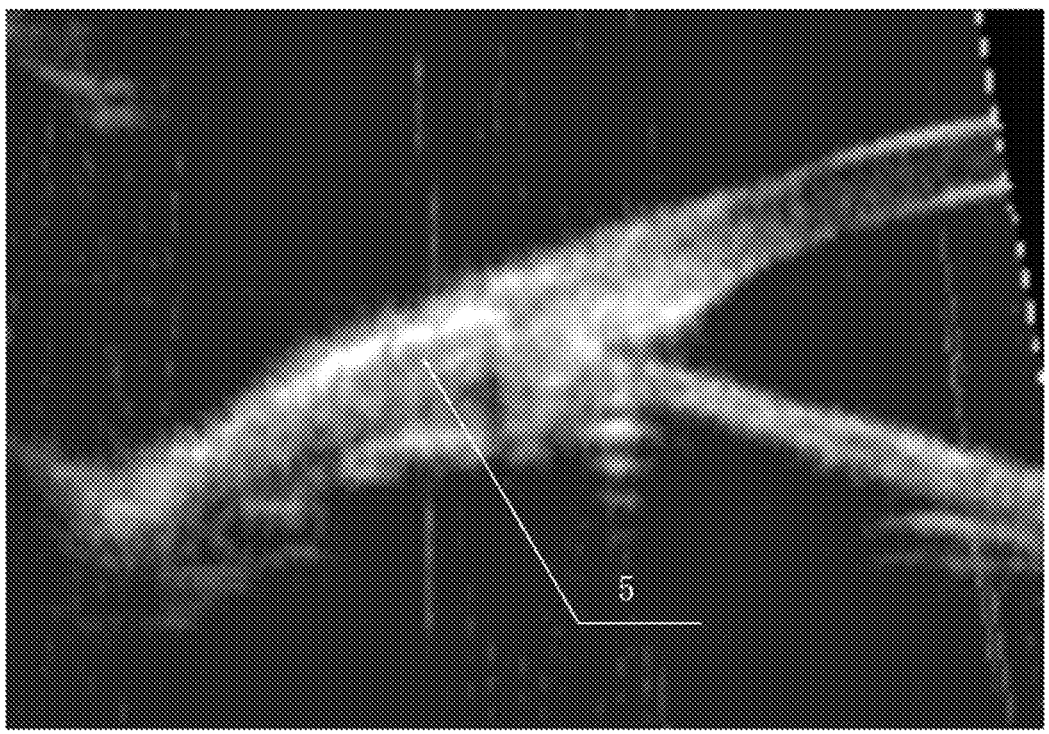

FIG. 7 is the anterior segment photographs 6 months after the surgery of the present invention; wherein FIG. 7A is the image of the slit lamp microscopy showing the scleral wounds; FIG. 7B is the UBM image showing the centration of the lens; FIG. 7C is the UBM image showing the intraocular lens haptic in the sclera.

DETAILED DESCRIPTION

The present invention now will be further illustrated in combination with FIG. 1, FIG. 2A, FIG. 2B, FIG. 3, FIG. 4, FIG. 5A, FIG. 5B, FIG. 6, and FIG. 7A, FIG. 7B, FIG. 7C.

Referring to FIGS. 1-5, after anesthetization, for patients not undergoing vitreous surgery, conventional vitrectomy or anterior vitrectomy was conducted in advance, a lateral corneal incision 1 was made at the position of 2 o'clock and a perfusion tube 100 was inserted into the anterior chamber 401, two conjunctival incisions 103 of 3.0 mm were cut on the conjunctiva 102 outside the margin of cornea 104 (See, e.g., FIGS. 2A, 2B and 5B), at the positions of 4 o'clock and 10 o'clock respectively; two puncture openings 2 were made at the position of 4 o'clock, in a distance of 1.5-2.0 mm outside the margin of cornea 104 with a 26 G pinhead, forming two puncture channels 201, the spacing distance between the two puncture openings 2 was 1 mm, the puncture openings 2 were parallel to the margin of cornea 104 and formed an angle of 30° with the surface of the sclera, the puncture directions of the two puncture openings 2 were opposite, making the puncture channels 201 profiled in a splayed pattern, and a lamellar sclera incision 202 was cut in the distance of 1 mm between the two puncture openings 2, forming a groove 3; and then the same processes were conducted at the symmetrical position of 10 o'clock, as shown in FIG. 1.

Figure 2A:
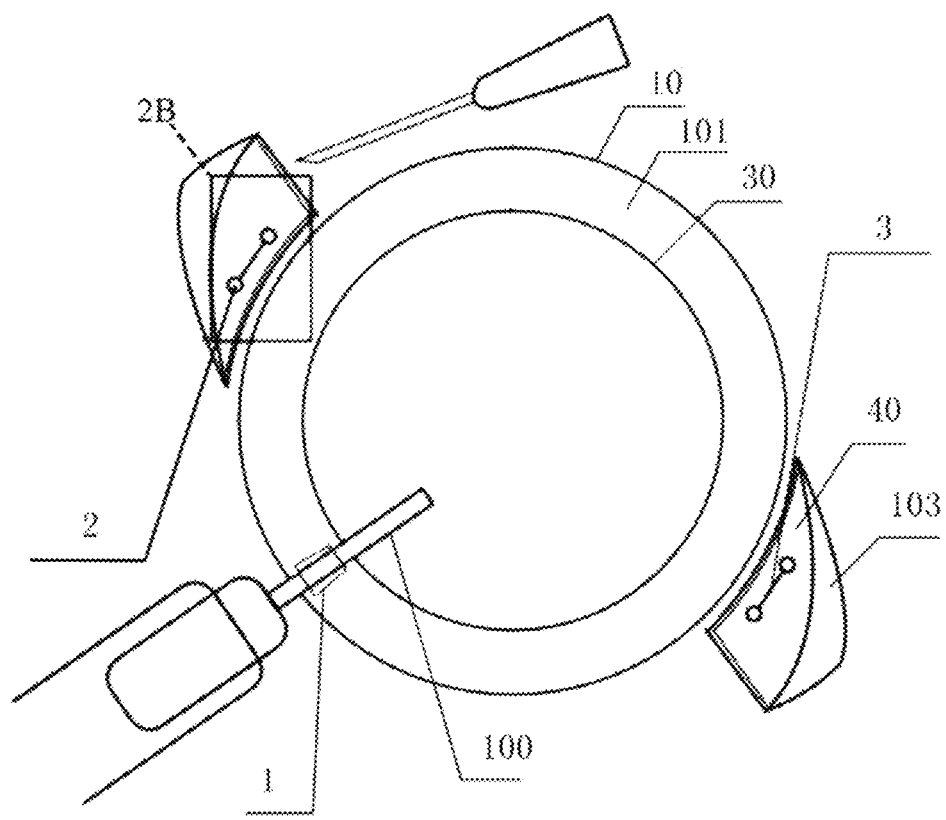
FIG. 2A is the graphical representation of surgical procedures of the present invention.
Figure 2B:
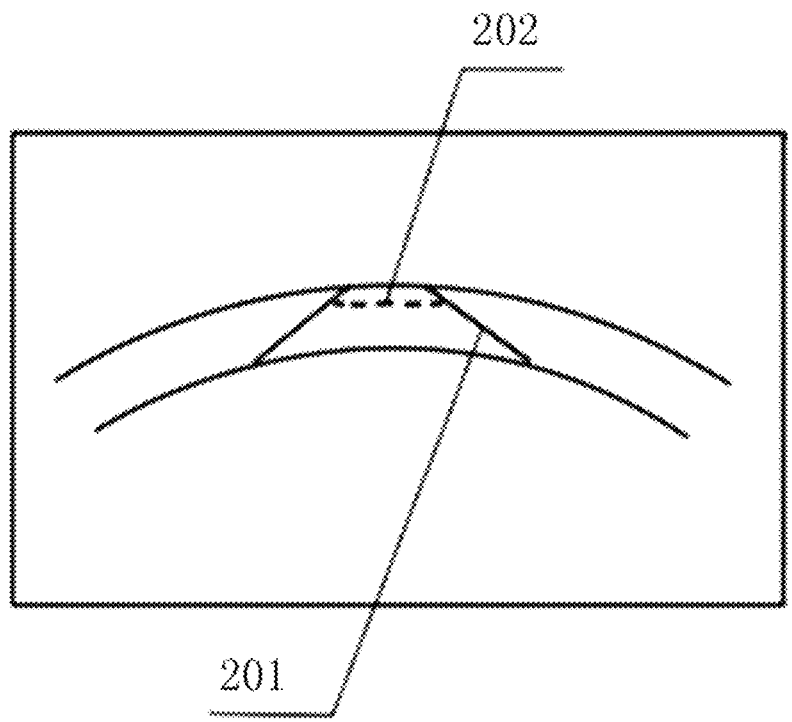
FIG. 2B is an enlarged view of a portion of FIG. 2A.

A main corneal incision 4 of 3.0 mm was made over the cornea 104, through which the intraocular lens 403 was pushed into the anterior chamber 401, leaving one haptic 5 outside the main corneal incision 4, a 25 G membrane forceps 402 went into the eye from the puncture opening 2 on one side, grasping one haptic 5 of the intraocular lens 403 and pulling it out of the eye through one puncture opening 2, similarly the other haptic 5 of the intraocular lens 403 was grasped from the puncture opening 2 on the other side at the position of 10 o'clock and pulled out of the eye through the puncture opening 2 on this side; as shown in FIGS. 2A and 2B.

Figure 3:
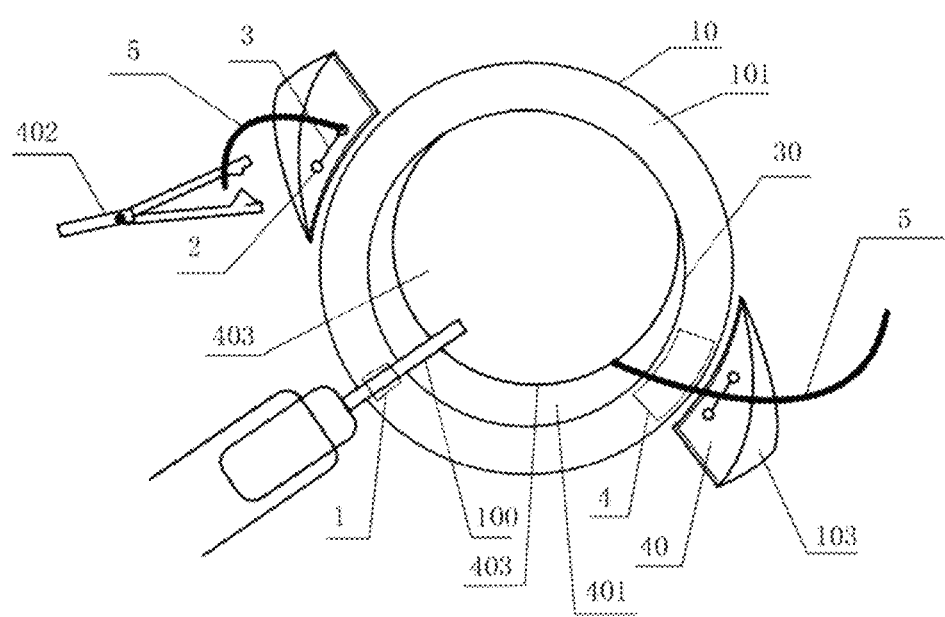
FIG. 3 is the graphical representation of surgical procedures of the present invention.

The haptic 5 fixed outside the eye was bent and then folded back into the vitreous chamber 501 through the adjacent puncture opening 2, just leaving the haptic 5 of the intraocular lens 403 exposed outside the sclera embedded in the groove 3 formed by the lamellar sclera incision 202 between two adjacent puncture openings 2; as shown in FIG. 3.

Figure 4:
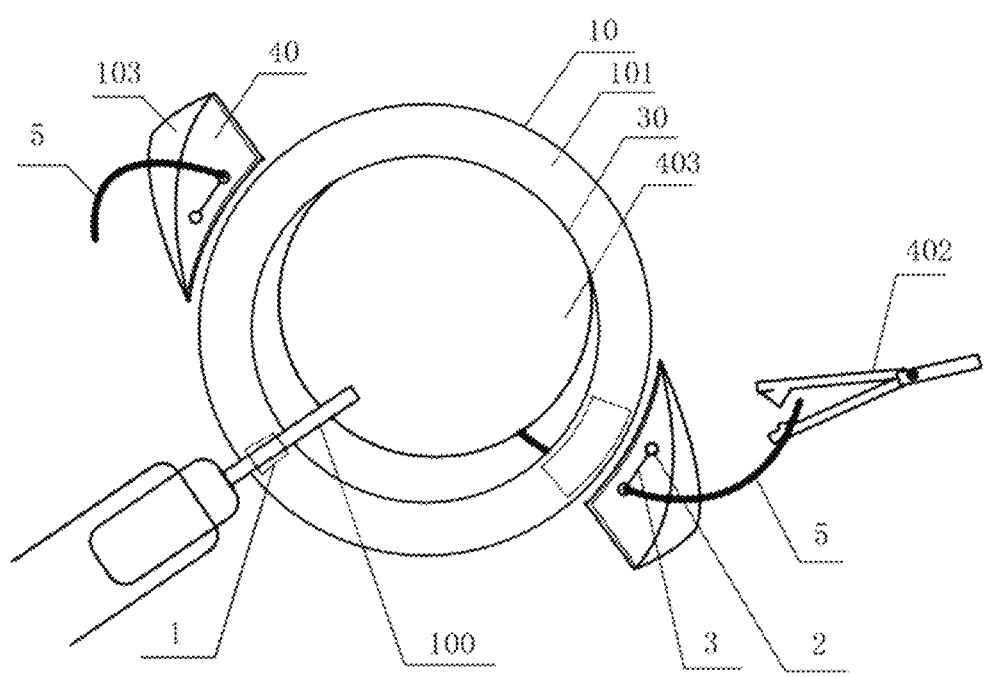
FIG. 4 is the graphical representation of surgical procedures of the present invention.

The lens haptic 5 looks like a fishhook as shown in the figures, with the tip in the vitreous chamber 501; as shown in FIG. 4.

Figure 5A:
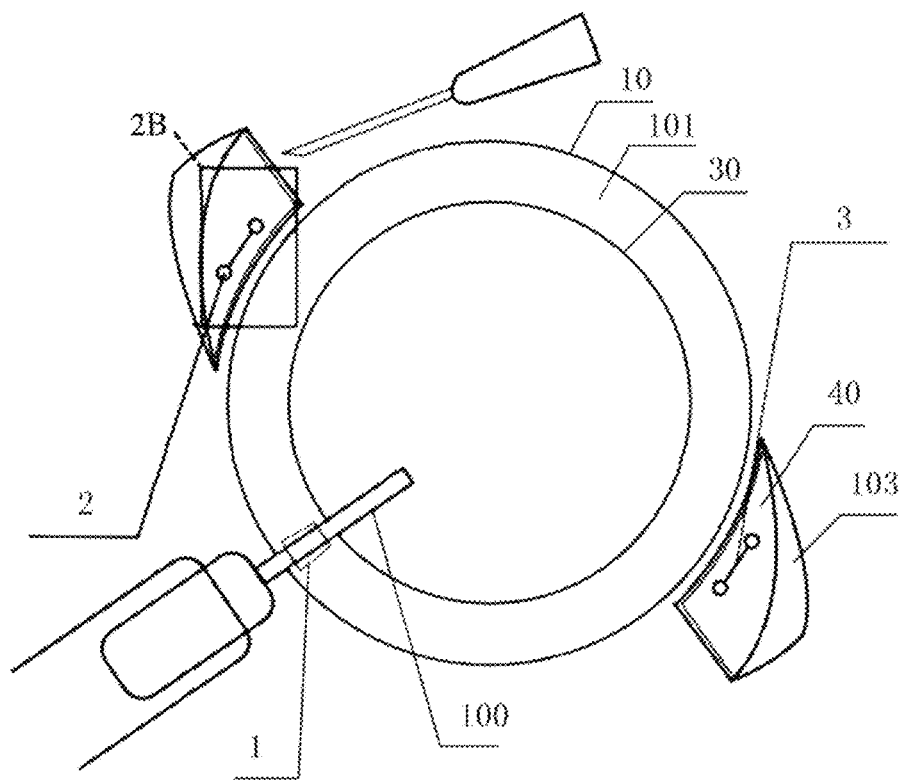
FIG. 5A is the graphical representation of surgical procedures of the present invention.
Figure 5B:
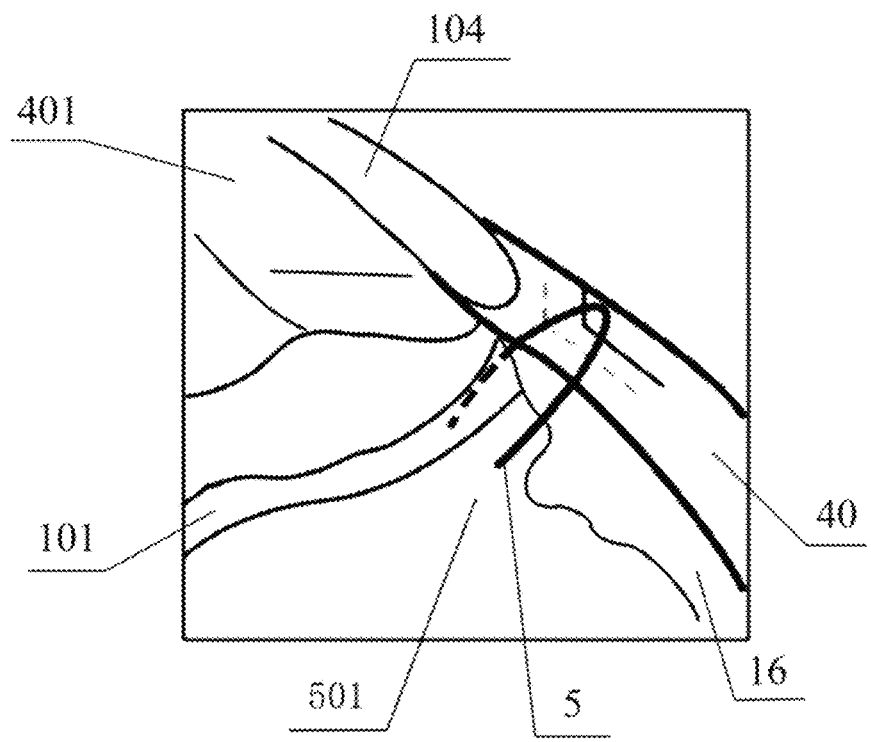
FIG. 5B is an enlarged view of a portion of FIG. 2A.

The main corneal incision 4 was watertight, the conjunctival incisions 103 were sewed with absorbable suture to complete the implantation and fixation of the intraocular lens 403 in the vitreous chamber 501, as shown in FIGS. 5A and 5B.

FIG. 7B depicts lens 403 adjacent iris 101 in vitreous chamber 501.

The fact that the haptic 5 of the intraocular lens 403 could be bent smoothly and folded back into the vitreous chamber 501 was related to the use of Matrix AcrylicAurium 400 intraocular lens 403 in the operation, wherein the haptic 5 employed polyvinylidene fluoride (PVDF), which was in a revised C shape, and formed an angle of 5° with the lens body. Finally, the main corneal incision 4 was watertight, the conjunctival incisions 103 were sewed with 8-0 absorbable suture.

Figure 6:
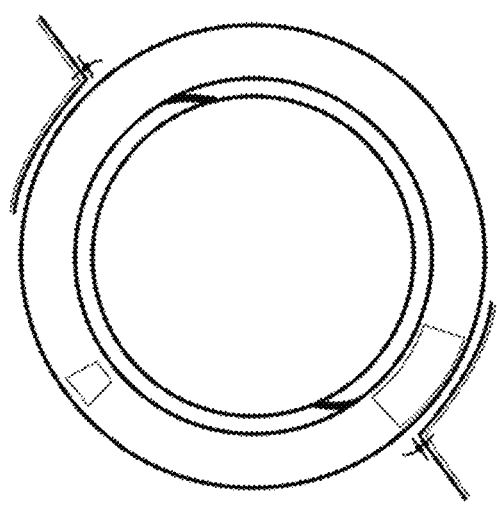
FIG. 6 is the graphical representation of surgical procedures of the present invention.

Our improved technique was conducted in 15 patients. This technique, in combination with vitrectomy, has removed the vitreous bodies of all patients partially or completely. The average preoperative BCVA is 0.82 log MAR units, and is 0.44 log MAR units in the follow-up visit after 6 months (Table 1). The follow-up visit after the patients come back shows good lens center and stable tactile fixation (FIG. 6). In the follow-up inspection after 6 months, there were no complications such as postoperative inflammation, hyphema, decentration, glaucoma, corneal edema, or wound leakage, etc. observed (Table 2). No eyes needed the subsequent surgery.

TABLE 1

Baseline characteristics and postoperative data of the patients

| Characteristics | Data |
|---|---|
| Number of eyes (Number of patients) | 17 (15) |
| Age, years | 56.4 ± 13.5 |
| Male/female, n | 7/8 |
| Preoperative visual acuity | 0.82 ± 0.89 |
| Postoperative visual acuity at 6 months[a] | 0.44 ± 0.45 |
| Preoperative intraocular pressure, mmHg | 18.0 ± 3.0 |
| Postoperative intraocular pressure at 1 week, mmHg[a] | 14.8 ± 7.2 |
| Postoperative intraocular pressure at 6 months, mmHg[a] | 17.1 ± 2.9 |

All values stands mean ± standard deviation

BCVA = best corrected visual acuity;

IOP = intraocular pressure.

[a] compared by Fisher exact test;

others compared by two-paired test.

TABLE 2

Clinical features and postoperative surgical outcome of each eyes

| Cases | Gender/Age | Operated Eye | Associated ocular conditions from previous surgery | Type of dislocation at presentation | Preoperative logMAR BCVA | Postoperative logMAR BCVA at 6 months | Postoperative complications |
|---|---|---|---|---|---|---|---|
| 1 | M/53 | Right | PCR and sulcus-fixated IOL | Out-of-the-bag | 0.22 | 0.50 | None |
| 2 | M/46 | Right | PCR and sulcus-fixated IOL | In-the-bag | 1.30 | 1.30 | None |
| 3 | M/24 | Left | PCR and sulcus-fixated IOL | Out-of-the-bag | 0.22 | 0.22 | None |
| 4 | M/48 | Right | PCR and sulcus-fixated IOL | Out-of-the-bag | 0.05 | 0 | None |
| 5 | M/48 | Left | Marchesani Syndrome, subluxated crystalline lens | In-the-bag | 0.10 | 0 | None |
| 6 | M/75 | Left | Trauma, aphakic | Absence of capsular bag | 2.60 | 1.30 | None |
| 7 | M/58 | Left | Trauma, aphakic | Absence of capsular bag | 0.10 | 0.22 | None |
| 8 | F/53 | Left | Trauma, luxated crystalline lens | Out-of-the-bag | 0.40 | 0.52 | None |
| 9 | F/59 | Right | PCR and sulcus-fixated IOL | Out-of-the-bag | 2.30 | 0.40 | None |
| 10 | F/59 | Left | PCR and sulcus-fixated IOL | Out-of-the-bag | 2.60 | 0.22 | None |
| 11 | F/69 | Right | PCR and sulcus-fixated IOL | Out-of-the-bag | 0.70 | 0.70 | None |
| 12 | M/72 | Left | Subluxated crystalline lens | In-the-bag | 1.00 | 0.10 | None |
| 13 | F/35 | Right | Subluxated crystalline lens | In-the-bag | 0.40 | 0.40 | None |
| 14 | F/60 | Right | Luxated crystalline lens | In-the-bag | 0.10 | 0.15 | None |
| 15 | F/68 | Right | Subluxated crystalline lens | In-the-bag | 1.00 | 0.52 | None |
| 16 | F/60 | Left | Subluxated crystalline lens | In-the-bag | 0.00 | 0.00 | None |
| 17 | F/71 | Right | Luxated crystalline lens | In-the-bag | 0.80 | 1.30 | None |

BCVA = best corrected visual acuity; PCR = posterior capsule rupture.

The method of sutureless intrascleral haptic-hook lens implantation proposed in the present invention may be adapted to patients in need of intraocular lens 403 implantation while without sufficient capsular support, such as aphakia, intraocular lens 403 or lens dislocation, etc. This method enhances the stability and centrality of the lens, the surgical procedures are simple and easy to master, which reduces the operation time. In the cases implemented currently, we have not found the complications such as incision leakage, retinal detachment, endophthalmitis, tilt or dislocation of the intraocular lens 403, vitreous hemorrhage, and the like, and the postoperative visual acuities of patients have been significantly improved.

It should be understood to persons skilled in the relevant art that the present invention has been described following the above detailed description, while the inventive ideas of the present invention were not restricted to the present invention, and any variations employing the ideas of the present invention should be included in the protection scope of the claims.

The above descriptions were only the preferred embodiments of the present invention, the protection scope of which should not be limited by the above embodiments, and all technical schemes within the spirit of the present invention all belong to the protection scope of the present invention. It should be noted to persons of ordinary skills in the art that several improvements and modifications without departing from the principle of the present invention also should be deemed as the protection scope of the present invention.

What is claimed is:

1. A method of sutureless intrascleral haptic-hook lens implantation in an eye, comprising the following steps:
    (1) making a lateral corneal incision and inserting a perfusion tube into the anterior chamber, cutting two opposing conjunctival incisions, including a first conjunctival incision and a second conjunctival incision, of 3.0 mm each, on the conjunctiva outside a margin of the cornea, at a first conjunctival region and at a second conjunctival region, respectively, the first conjunctival region being diametrically opposite to the second conjunctival region across the cornea;
    (2) making first and second puncture openings in the conjunctiva at the first conjunctival region at 1.5-2.0 mm outside the margin of the cornea, respectively forming a first puncture channel and a second puncture channel, a spacing distance between the first and second puncture openings being 1 mm, and cutting a first lamellar sclera incision between the first and second puncture openings, thereby forming a first groove between the first and second puncture openings;
    (3) repeating step (2) at the second junctival location by making first and second puncture openings in the conjunctiva at the second conjunctival region at 1.5-2.0 mm outside the margin of the cornea, respectively forming a first puncture channel and a second puncture channel at the second conjunctival region, a spacing distance between the first and second puncture openings at the second conjunctival region being 1 mm, and cutting a second lamellar sclera incision between the first and the second puncture openings at the second conjunctival region, thereby forming a second groove between the first and second puncture openings at the second conjunctival region;

(4) making a main corneal incision of 3.0 mm over the cornea, and pushing an intraocular lens through the main corneal incision and into the anterior chamber, leaving an end of a first haptic of the intraocular lens outside the main corneal incision, introducing a membrane forceps into the eye through the first puncture opening at the second conjunctival region, grasping a second haptic of the intraocular lens and pulling a portion of said second haptic out of the eye through the first puncture opening at the second conjunctival area, grasping the first haptic of the intraocular lens via the first puncture opening at the first conjunctival region and pulling the first haptic out of the eye through the first puncture opening at the second conjunctival area;

(5) bending the first haptic and then folding the bent first haptic back into the vitreous chamber through the second puncture opening at the first conjunctival region, just leaving a portion of the first haptic of the intraocular lens exposed outside the sclera and embedded in the groove formed by the lamellar sclera incision between the first and second puncture openings at the first conjunctival region, and bending the second haptic and then folding the bent second haptic back into the vitreous chamber through the second puncture opening at the second conjunctival region, just leaving a portion of the second haptic of the intraocular lens exposed outside the sclera and embedded in the groove formed by the lamellar sclera incision between first and second puncture openings at the second conjunctival region, thereby securing the lens in the vitreous chamber;

(6) removing the perfusion tube and closing the conjunctival incisions to complete the implantation and fixation of the intraocular lens.

2. The method of sutureless intrascleral haptic-hook lens implantation according to claim 1, wherein a first pair of puncture openings that are the first and second puncture openings at the first conjunctival region are at a 4 o'clock position of a theoretical clock dial superposed the eye and having a 12 o'clock position at a topmost portion of the eye and a 6 o'clock position at a bottommost portion of the eye, and a second pair of puncture openings that are the first and second puncture openings at the second conjunctival region are at a 10 o'clock position of the theoretical clock face.

3. The method of sutureless intrascleral haptic-hook lens implantation according to claim 1, wherein the first and second conjunctival incisions are set at the positions of 4 o'clock and 10 o'clock, respectively, on a theoretical clock dial superposed the eye and having a 12 o'clock position at a topmost portion of the eye and a 6 o'clock position at a bottommost portion of the eye.

4. The method of sutureless intrascleral haptic-hook lens implantation according to claim 1, wherein the intraocular lens is a 3-piece posterior chamber intraocular lens, the haptics of which comprises polyvinylidene fluoride (PVDF)-g, and each haptic is in a C shape, forming an angle of 5° with a lens body.

5. The method of sutureless intrascleral haptic-hook lens implantation according to claim 1, wherein the conjunctival incisions in step (6) are closed by electrocoagulation.

6. The method of sutureless intrascleral haptic-hook lens implantation according to claim 1, wherein the first and second puncture channels in step (2) form an angle of 30° with a surface of the sclera, the puncture channels being profiled in a splayed pattern.

7. The method of sutureless intrascleral haptic-hook lens implantation according to claim 1, further comprising adjusting the first or the second haptic to cause the intraocular lens to be centered.

8. The method of sutureless intrascleral haptic-hook lens implantation according to claim 1, wherein respective puncture directions of the two puncture channels of the first and second puncture openings at the first conjunctival regions form a splayed pattern.

* * * * *